(12) United States Patent
Lipscombe et al.

(10) Patent No.: US 8,043,824 B2
(45) Date of Patent: Oct. 25, 2011

(54) METHODS FOR DETERMINING THE REDOX STATUS OF PROTEINS

(75) Inventors: Richard J. Lipscombe, Perth (AU); Peter G. Arthur, Wembley (AU); James K. Lui, Winthrop (AU)

(73) Assignee: Proteomics International Pty Ltd., West Perth (AU)

( * ) Notice: Subject to any disclaimer, the term of this patent is extended or adjusted under 35 U.S.C. 154(b) by 598 days.

(21) Appl. No.: 12/154,467

(22) Filed: May 22, 2008

(65) Prior Publication Data

US 2008/0305495 A1    Dec. 11, 2008

Related U.S. Application Data

(63) Continuation of application No. PCT/AU2006/001757, filed on Nov. 21, 2006.

(51) Int. Cl.
*G01N 33/53*    (2006.01)
*G01N 31/00*    (2006.01)

(52) U.S. Cl. ............ 435/7.21; 435/7.1; 436/1; 436/501; 436/518; 424/9.1; 424/520; 422/50; 530/300; 530/350

(58) Field of Classification Search .................. None
See application file for complete search history.

(56) References Cited

OTHER PUBLICATIONS

Sahaf, B et al. Proceedings of the National Academy of Sciences (USA) 2003, vol. 100, No. 7, pp. 4001-4005.
Nishi, T et al. The Journal of Biological Chemistry, 2002, vol. 277, No. 46, pp. 44548-44556.

*Primary Examiner* — Lisa Cook
(74) *Attorney, Agent, or Firm* — Richard B. Emmons; Kathleen Williams; Edward Angell Palmer & Dodge LLP

(57) ABSTRACT

A method for determining the redox status of a protein sample, the method comprising the steps of: a) contacting the sample with a first label adapted to bind to at least one reduced cysteine group therein; b) contacting the sample with a reducing agent to reduce at least one oxidized cysteine group therein; c) contacting the sample with a second label adapted to bind to any reduced cysteine groups produced in step (b); and d) determining the ratio of the signal from the first label to the signal from the second label wherein the ratio indicates the redox status.

38 Claims, 8 Drawing Sheets

A

B

C

A

B

C

METHODS FOR DETERMINING THE REDOX STATUS OF PROTEINS

RELATED APPLICATIONS

This is a continuation patent application that claims priority to PCT patent application number PCT/AU2006/001757, filed on Nov. 21, 2006, which claims priority to Australian patent application number. 2005906469, filed on Nov. 22, 2005, the entirety of which are herein incorporated by reference.

FIELD OF THE INVENTION

The present invention relates to a method for determining the redox status of a protein. The invention also relates to a method for detecting protein modification, particularly modification caused by reactive oxygen specifies (ROS) and to kits and other uses of the methods described herein.

BACKGROUND ART

The term reactive oxygen species (ROS) is a generalized description for a collection of reactive oxygen molecules of biological significance. These include: superoxide ($O_2$), hydroxyl radical (OH.), peroxyl radical (ROO), alkoxyl radical (RO), hydroperoxyl radical (HOO), hypochlorous acid (HOCl), hydrogen peroxide ($H_2O_2$), ozone ($O_3$), singlet oxygen ($^1O_2$) and peroxinitrite (ONOO).

ROS are often though of as being directly detrimental to cell viability because they can irreversibly damage key macromolecules such as proteins, nucleic acids and lipids. however there is now evidence that low levels of at least one ROS, hydrogen peroxide ($H_2O_2$) has been implicated in the regulations of signal transduction pathways linked to the control of cell proliferation, cell growth and cell death.

ROS, particularly those with mild oxidant capabilities, form suitable signaling molecules as they are capable of oxidizing the reduced thiol groups of cysteine residues to form disulfide bonds with glutathione, an adjacent cysteine residue or a small protein such as thioredoxin. This mild and reversible oxidation is referred to as thiol group modification. As ROS levels increase, more thiol groups become oxidized to disulfides. Consequently, the ratio of reduced groups (thiols) to oxidized groups (disulfide) is a measure of the redox status of proteins, cells or tissues.

Once oxidised, thiol group modifications can be reversed or reduced by specialised enzyme systems, such as thioredoxin or glutaredoxin. This reversible modification of a protein's cysteines between an oxidised and reduced state is analogous to the regulation of a protein's function by phosphorylation/dephosphorylation. Changes in the redox status of a protein, involving disulfide formation and glutathionylation, have been shown to affect the activity of several different signalling transduction proteins and it is thought that changes in the thiol redox status may influence many aspects of cell function, viability and survival.

Mammalian tissues are rich in protein thiols (20-40 mM) and many intracellular proteins have been identified that can undergo thiol group modification. However, despite great interest, only in a few cases has the biological significance of these modifications been identified. This is in part due to a poor understanding of the complexity of the system, a lack of knowledge of the relationship between the thiol redox system and other antioxidant systems and the difficulty in identifying specific biological effects. For example, it is difficult to establish that specific thiol group modifications exist in vivo and are not simply a manifestation of the unnatural oxidising conditions of in vitro systems.

Furthermore, the current methods for determining the redox status of biological systems e.g. proteins, cells, tissues in vivo (and even in vitro) lack sufficient sensitivity, reproducibility or specificity and do not allow the detailed investigation of the effects of changes in redox status on cell function, viability and survival. The current methods fall into two main categories and are discussed further below.

Methods Based on Total Redox Changes

One method involves reacting reduced thiol groups of proteins with groups such as DTNB or Ellman's reagent (for colorimetric determination), bromobimane (for fluorescence based determination) or groups that result in signal amplification (papain). However, most (greater than 90%) of the cysteine residues on a protein are in the reduced thiol form. Therefore, techniques must be very sensitive to detect the difference between, for example, 90% reduced cysteine and 95% reduced cysteine. A more sensitive assessment of thiol redox changes comes from measuring the oxidised disulfides, but this increases the complexity of the method. Furthermore, such methods of measuring oxidised disulfides are not particularly precise and are technically demanding and time consuming.

A second approach to measuring changes in thiol groups is indirect and involves assessing the ratio of oxidised glutathione (GSSG) to reduced glutathione (GSH). Glutathione is the substrate for several antioxidant enzymes. The underlying assumption is that changes in the GSSG/GSH ratio will reflect changes in the reduction status of the cysteine groups on a protein. However, the glutathione system can act independently of the thioredoxin thiol reduction system. Furthermore, the GSSG/GSH analytical techniques are not suitable for the analysis of mitochondria, cells or tissues where only limited sample is available.

Additionally, the above methods rely on the determination of the relative abundance of reduced or oxidised cysteine residues relative to the amount of protein in the sample. The relatively poor precision of protein assays reduces the precision in assessing thiol redox changes.

Methods Involved with Measuring Specific Protein Changes

A third approach to the analysis of thiol redox changes uses a "one label" approach and polyacrylamide gel electrophoresis (PAGE). Generally, this involves attaching or reacting one label, such as a radioactive label, to the reduced thiol groups and measuring the relative amount of labelled residues compared to the total amount of protein. Alternatively, the reduced thiol groups initially present on a protein are blocked and then the protein is exposed to a reducing agent. A label, such as a radioactive label, is then attached to the thiol groups that have been generated following the reduction of any groups that were initially in the oxidised disulfide state. However, this method does not allow the concurrent measurement of both the reduced and oxidised cysteine residues of a protein.

The lack of precision of this approach is further accentuated by variations inherent with PAGE and other systems for visualising the results of the methods. This greatly reduces the practical utility of these methods where only one signal is measured at a time.

The present invention seeks to address or at least partially ameliorate the problems attendant with the prior art.

SUMMARY OF THE INVENTION

The present invention provides a method for determining the redox status of a protein sample, the method comprising the steps of:

a) contacting the sample with a first label adapted to bind to at least one reduced cysteine group therein;
b) contacting the sample with a reducing agent to reduce at least one oxidised cysteine group therein;
c) contacting the sample with a second label adapted to bind to any reduced cysteine groups produced in step (b); and
d) determining the ratio of the signal from the first label to the signal from the second label wherein the ratio indicates the redox status.

The present invention provides a means for determining the redox status of new proteins or proteins that have been treated or modified from their naturally occurring redox status. Such information could be assembled into a useful database. Such a database could be used to generate a protein or antibody array targeted to monitor proteins undergoing thiol redox changes. Thus, the present invention also provides a database containing one or more redox values obtained using the method of the invention.

The present invention also provides a method for determining whether a protein sample has been modified by a protein modifying agent, the method comprising the steps of:
a) contacting the sample with a first label adapted to bind to at least one reduced cysteine group therein;
b) contacting the sample with a reducing agent to reduce at least one oxidised cysteine group therein;
c) contacting the sample with a second label adapted to bind to any reduced cysteine groups produced in step (b); and
d) determining the ratio of the signal from the first label to the signal from the second label and using said ratio to determine if the protein sample has been modified.

The present invention also provides a method for determining whether a protein sample has been modified, the method comprising the steps of:
a) contacting the sample with a first label adapted to bind to at least one reduced cysteine group therein;
b) contacting the sample with a reducing agent to reduce at least one oxidised cysteine group therein;
c) contacting the sample with a second label adapted to bind to any reduced cysteine groups produced in step (b); and
d) determining the ratio of the signal from the first label to the signal from the second label and comparing the ratio to a reference ratio to determine if the sample has been modified.

The method of the present invention may be conveniently performed using a kit comprising a series of reagents necessary to carry out the method. Thus, the present invention also provides a kit for treating a protein sample comprising:
a) a first label adapted to bind to at least one reduced cysteine group in the protein sample;
b) a reducing agent capable of reducing at least one oxidised cysteine group in the sample; and
c) a second label adapted to bind to any reduced cysteine groups produced after use of the reagent in part (b).

An application of the method of the present invention is the determination of protein modification caused by ROS. ROS are common causative agents for many important pathologies such as stroke, heart attack and age-related degeneration. Thus, the present invention also provides a useful means for assessing ROS associated pathologies and other pathologies at the protein level. Thus, the present invention also provides a method for assessing a ROS associated pathology in a subject, the method comprising the steps of a) contacting a protein sample from the subject with a first label adapted to bind to at least one reduced cysteine group therein;
b) contacting the sample with a reducing agent to reduce at least one oxidised cysteine group therein;
c) contacting the sample with a second label adapted to bind to any reduced cysteine groups produced in step (b); and
d) determining the ratio of the signal from the first label to the signal from the second label and using said ratio to determine if the sample has been modified.

The method of the present invention could also be used to assess the effects of therapeutic interventions for ROS associated pathologies. Thus, the present invention also provides a method for assessing the efficacy of a therapeutic intervention for a ROS associated pathology in a subject, the method comprising the steps of:
a) contacting a protein sample from the subject with a first label adapted to bind to at least one reduced cysteine group therein;
b) contacting the sample with a reducing agent to reduce at least one oxidised cysteine group therein;
c) contacting the sample with a second label adapted to bind to any reduced cysteine groups produced in step (b); and
d) determining the ratio of the signal from the first label to the signal from the second label and comparing said ratio obtained in the absence of the intervention with the ratio obtained in the presence of the intervention.

BRIEF DESCRIPTION OF THE DRAWINGS

FIG. 1 shows ProXpress fluorescence scans of an SDS-PAGE gel of protein samples extracted from 2 mM $H_2O_2$ treated Jurkat cells (Treated) and untreated Jurkat cells (Control). Proteins, labelled using the 2 detectable label method of the present invention were electrophoresed in 1D and then the two strips corresponding to the respective samples were run side by side on a 20 cm×20 cm SDS-PAGE for 2D. The images show that oxidation of protein thiols can be detected using combination of TMR and Sypro Ruby.

FIG. 2A shows TMR scan of the 2D SDS-PAGE, FIG. 2B shows the same gel scanned at FL wavelengths while FIG. 2C is a merged image of FIGS. 2A and B.

DETAILED DESCRIPTION OF THE INVENTION

Figure 1A:
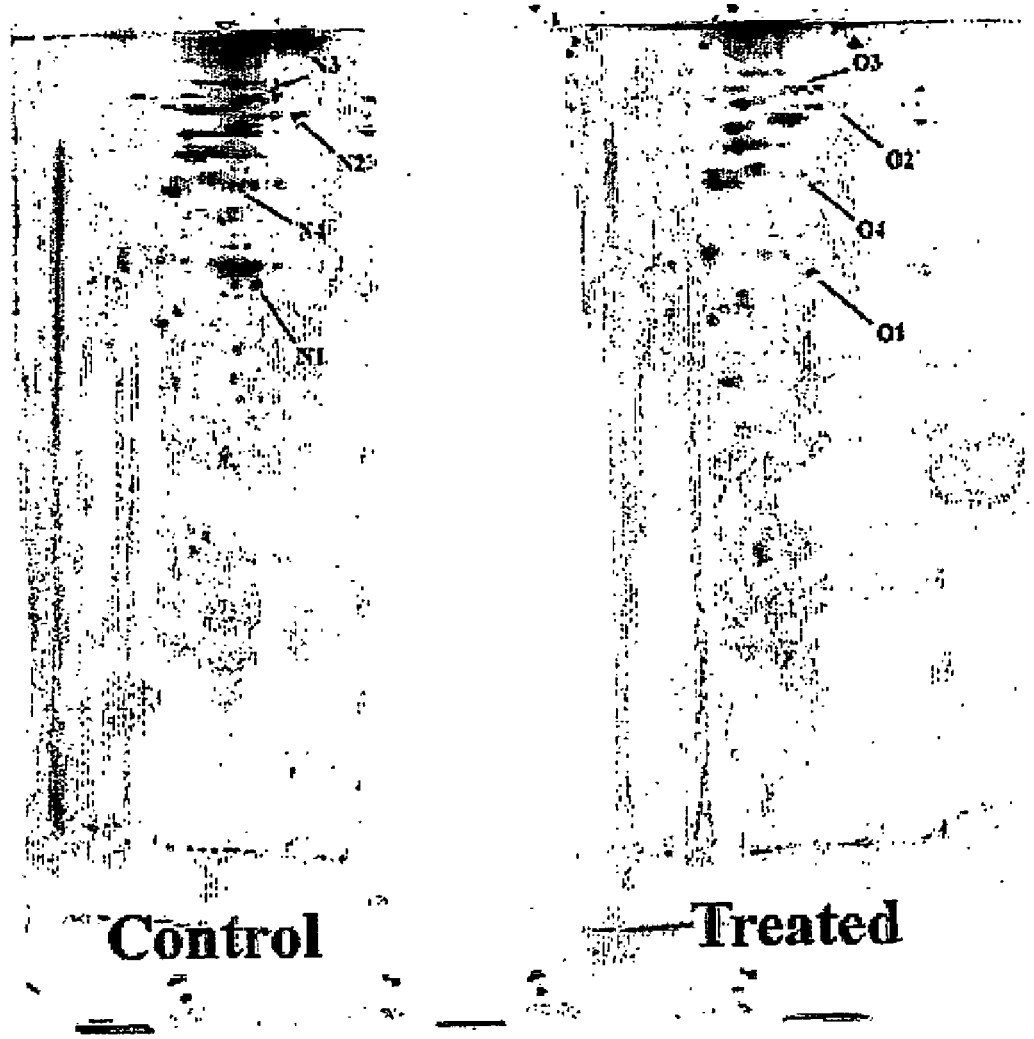
FIG. 1A is the TMR scan of the gel whilst

Determining the Redox Status of a Protein Sample

The present invention also provides a method for determining the redox status of a protein sample, the method comprising the steps of:
  a) contacting the sample with a first label adapted to bind to at least one reduced cysteine group therein;
  b) contacting the sample with a reducing agent to reduce at least one oxidised cysteine group therein;
  c) contacting the sample with a second label adapted to bind to any reduced cysteine groups produced in step (b); and
  d) determining the ratio of the signal from the first label to the signal from the second label wherein the ratio indicates the redox status.

The method of the present invention allows for the redox status to be conveniently and accurately determined. The use of ratios rather than absolute values improves the sensitivity of the method as it enables relatively small changes in redox status to be determined. Another important advantage of the present invention is that the ratio can be measured on the same protein.

The method of the invention also overcomes many of the sample variability problems associated with other protein labelling methods for determining redox status. In this regard, the reliability of other proteomic techniques is further reduced by imprecision or "noise" caused by, for example, variation in protein extraction and loading as well as gel to gel variation. For example, even if different amounts of total protein were loaded on gels for two samples, it is still possible to compare those samples, as the within sample ratio of the two labels can be compared.

The protein sample may be varied and includes single proteins and mixtures of proteins. When the sample contains more than one protein the method of the present invention can be used to produce a profile that indicates which proteins in a sample have been modified and which ones have remained unchanged. Preferably, the sample is a cell extract or some other preparation derived from biological material such as a tissue sample or extract thereof. The sample can also be part of a cell such a sample containing mitochondria or another sub-cellular organelle.

For some applications of the method it may be beneficial to "fix" the sample prior to further treatment to prevent interchange between reduced and oxidised cysteine groups and thus ensure a representative sample is obtained. For example, the redox status of a protein may be changed during the extraction and purification of the protein from its native environment. Thus, the invention may further comprise the step of protecting reduced cysteine groups prior to labelling.

Preferably, the protection is achieved by quenching all thiol-disulfide reactions. The quenching can be carried out by treating the cells and acid trapping the proteins with an appropriate buffer such as the RQB buffer (trichloracetic acid (TCA) in acetone). Other methods of quenching thiol-disulfide reactions are known to those skilled in the art and may be used in the present method.

The reduced cysteine group may be varied and is preferably a thiol group such as Cys-SH (cysteine residue) or Cys-SOH (sulfenic acid residue).

The oxidised cysteine group may be varied and is preferably selected from the group comprising: Cys-S—S—X; wherein S—X could be from the same protein, another protein or a small molecular mass thiol such as glutathione, Cys-$SO_2H$, sulfinic acid; Cys-$SO_3H$, or sulfonic acid.

The first and second labels must be capable of being detected. It will also be appreciated that the labels should be compatible in that their respective signals should not unduly interfere with each other and are capable of being measured separately. Preferably, the signals from the labels do not interfere with each other at all. However, with this in mind, the particular labels used in the present invention may be varied provided they are capable of binding to a reduced cysteine group.

Preferably the labels emit distinguishable signals so that the relevant ratio can be determined. Even more preferably, the labels are adapted to bind to the same protein such that a single protein has both labels bound thereto.

In one form the labels include a component adapted to bind, preferably covalently, to a reduced cysteine group and a component capable of emitting a signal.

When the label includes a component adapted to bind to a reduced cysteine group, the component is preferably selected from the group consisting of: maleimide, phenylmercury, iodoacetamide, vinylpyridine, methyl bromide or iodoacetate or derivatives thereof. Preferably, this component is iodoacetamide or maleimide or a derivative thereof. When this component is iodoacetamide or maleimide or a derivative thereof the label is preferably contacted with the protein sample at a pH of 7-8 and in particular about 7.5.

The component capable of emitting a signal may be varied and can be any tag that can be reacted and targeted by a unique label such as a labelled antibody. The component may be a radioactive tag or enzyme such as horseradish peroxidase or antibody or a protein or a peptide. Preferably, this component is capable of being measured e.g. visualised. More particularly, this component may be fluorescent. Suitable fluorescent components include fluorescein, tetramethylrhodamine, Cye 3, Cye5 and Texas red, BODIPY, Oregon Green, eosin, pyridyloxazole, benzoxadiazole; Lucifer yellow, Alexa Flur, rhodamine and NANOGOLD. The specific concentration of reagents used in the present method can be routinely determined by one skilled in the art.

In another form of the invention the labels include a component adapted to bind to a reduced cysteine group and a component capable of being detected directly. In this form of the invention the labels may be low molecular mass compounds that are adapted to be detected using mass spectrometry.

It will also be appreciated that the label may comprise a single component that is adapted to bind to a reduced cysteine group and be detected directly such as by mass spectrometry.

It is possible that the labels used in the method will interfere with each other and thus have a deleterious effect on the method. Thus, the method of the present invention may further comprise the step of removing or inactivating the first label prior to addition of the second label. Removal or inactivation of the label may be carried out in any one of a number of ways apparent to those skilled in the art. Preferably, the label is removed through the use of a column such as a Sephadex G-25 column or precipitation using an organic solvent such as ethanol. However, any method that selectively removes the label from the reaction mix will be suitable.

The reducing agent may be varied and may be selected from the group comprising: cyteine, reduced glutathione, β-mercaptoethanol, thioglycollic acid, tributylphosphine (TBP), 2-carboxyethylphosphine (TCEP), dithiothreitol, sodium borohydride and sodium hydrosulfite. When TCEP or TBP is used it can be used at a concentration of about 0.5-5 mM.

The ratio may be determined by any suitable means and the means for detecting the signal from the labels is dependent somewhat on the labels used. For example, if fluorescent labels are used then the ratio may be conveniently determined by visualising the proteins in the sample and then measuring the signal from the labels. One particularly useful visualising means is PAGE as the protein sample can be applied to PAGE and then the signals from the labels measured at particular protein bands on the gel. Dependent on the type of label, other visualising means include phospho-imaging or lumi-imaging.

Alternate techniques to PAGE are immunoprecipitation (where a single protein of interest is isolated), protein or antibody arrays (where a multitude of proteins are isolated on a protein chip), and mass spectrometry and/or chromatography, where single or total protein extracts are analysed (for example by multidimensional chromatography). Mass spectrometry and the protein or antibody arrays offer the opportunity to scan 10, 100 or even 1000s of proteins very rapidly very much like microarrays.

Preferably, the method further comprises comparing the ratio determined in the method of the present invention against a reference ratio to determine the relative redox status. The reference ratio may be a redox status determined from a previous experiment or could be part of a known database of redox statuses for a given protein or protein composition.

Whilst the redox status of many naturally occurring proteins may be known the present invention provides a means for determining the redox status of new proteins or proteins that have been treated or modified from their naturally occurring redox status. Such information could be assembled into a useful database. Such a database could be used to generate a protein or antibody array targeted to monitor proteins undergoing thiol redox changes. Thus, the present invention also provides a database containing one or more redox values obtained using the method of the invention.

Detection of Protein Modification

The ratio determined using the method of the present invention reflects the redox status of the protein sample and changes in the ratio for particular proteins is indicative of protein modification. Thus, the present invention also provides a method for determining whether a protein sample has been modified by a protein modifying agent, the method comprising the steps of:
 a) contacting the sample with a first label adapted to bind to at least one reduced cysteine group therein;
 b) contacting the sample with a reducing agent to reduce at least one oxidised cysteine group therein;
 c) contacting the sample with a second label adapted to bind to any reduced cysteine groups produced in step (b); and
 d) determining the ratio of the signal from the first label to the signal from the second label and using said ratio to determine if the protein sample has been modified.

The protein modifying agent may be varied and includes a ROS and nitric oxide (NO). It also includes an agent that generates or otherwise causes, decreases or increases the production of an ROS and/or NO.

When the protein modifying agent is a ROS it may be any reactive oxygen molecule capable of modifying aspects of normal cellular functioning. Preferably, the ROS is capable of oxidising reduced thiol groups of cysteine residues to form disulphide bonds with glutathione, an adjacent cysteine or a small protein such as thioredoxin. Even more preferably the ROS is selected from the group comprising: superoxide ($O_2^-$), hydroxyl radical (OH.), peroxyl radical (ROO.), alkoxyl radical (RO.), hydroperoxyl radical (HOO.), hypochlorous acid (HOCl), hydrogen peroxide ($H_2O_2$), ozone ($O_3$), singlet oxygen ($^1O_2$) and peroxinitrite (ONOO). In one particular form of the invention the ROS is $H_2O_2$.

The ratio determined according to the method of the present invention can be applied in various ways. For example, the ratio for one or more proteins of interest in a given protein sample that has been contacted with a protein modifying agent, such as a ROS, can be compared to one or more reference ratios that reflect the proteins naturally occurring redox status. Comparison of the ratios of the treated proteins with the reference ratios will indicate which proteins, if any, have been modified through contact with the ROS. Thus, the present invention also provides a method for determining whether a protein sample has been modified, the method comprising the steps of:
 a) contacting the sample with a first label adapted to bind to at least one reduced cysteine group therein;
 b) contacting the sample with a reducing agent to reduce at least one oxidised cysteine group therein;
 c) contacting the sample with a second label adapted to bind to any reduced cysteine groups produced in step (b); and
 d) determining the ratio of the signal from the first label to the signal from the second label and comparing the ratio to a reference ratio to determine if the sample has been modified.

Alternatively, treated and untreated (control) protein samples could be subjected to the method of the present invention concurrently. In this form of the invention the relative ratios of the treated and untreated protein samples can be used to assess protein modification.

Kits

The method of the present invention may be conveniently performed using a kit comprising a series of reagents necessary to carry out the method. Thus, the present invention also provides a kit for treating a protein sample comprising:
 a) a first label adapted to bind to at least one reduced cysteine group in the protein sample;
 b) a reducing agent capable of reducing at least one oxidised cysteine group in the sample; and c) a second label adapted to bind to any reduced cysteine groups produced after use of the reagent in part (b).

Preferably, the kit further comprises instructions to utilise the reagents according to the methods described herein. Even more preferably the kit further comprises instructions to determine the ratio of the signal from the first label to the signal from the second label. In one particular form of the invention the kit comprises a means to remove unbound first label e.g. a spin column.

Uses

As indicated above, one application of the method of the present invention is the determination of protein modification caused by ROS. ROS are common causative agents for many important pathologies such as stroke, heart attack and age-related degeneration. The present invention provides a useful means for assessing ROS associated pathologies and other pathologies at the protein level. Thus, the present invention also provides a method for assessing a ROS associated pathology in a subject, the method comprising the steps of
- a) contacting a protein sample from the subject with a first label adapted to bind to at least one reduced cysteine group therein;
- b) contacting the sample with a reducing agent to reduce at least one oxidised cysteine group therein;
- c) contacting the sample with a second label adapted to bind to any reduced cysteine groups produced in step (b); and
- d) determining the ratio of the signal from the first label to the signal from the second label and using said ratio to determine if the sample has been modified.

Preferably, the pathology is selected from the group comprising: stroke, heart attack and age-related degeneration. Some of the diseases likely to be associated with changes in thiol redox are: atherosclerosis, peripheral vascular occlusive disease, hypertension, alcoholic liver disease, angina, emphysema & bronchitis, chronic obstructive lung disease, Alzheimer's Disease, Parkinson's Disease, diabetes, cancer, organ transplantation such as liver transplantation related disease, coronary heart disease/heart failure, stroke/neurotrauma, cardiovascular disease, high blood pressure, hypoxia, fetal distress syndrome and sleep apnoea.

This method could be used to identify key protein modifications associated with a given pathology and hence identify novel therapeutic targets. Alternatively, the method could be used to characterise progression of the pathology at the protein level.

The method of the present invention could also be used to assess the effects of therapeutic interventions for ROS associated pathologies. Thus, the present invention also provides a method for assessing the efficacy of a therapeutic intervention for a ROS associated pathology in a subject, the method comprising the steps of:
- a) contacting a protein sample from the subject with a first label adapted to bind to at least one reduced cysteine group therein;
- b) contacting the sample with a reducing agent to reduce at least one oxidised cysteine group therein;
- c) contacting the sample with a second label adapted to bind to any reduced cysteine groups produced in step (b); and
- d) determining the ratio of the signal from the first label to the signal from the second label and comparing said ratio obtained in the absence of the intervention with the ratio obtained in the presence of the intervention.

The method of the present invention could also be used to follow changes in the redox state of proteins in a tissue over a period of time. For example, samples may be taken over a time course and analysed for changes in the redox status of proteins due to the supplements.

General

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in the specification, individually or collectively and any and all combinations or any two or more of the steps or features.

The present invention is not to be limited in scope by the specific embodiments described herein, which are intended for the purpose of exemplification only. Functionally equivalent products, compositions and methods are clearly within the scope of the invention as described herein.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

Throughout this specification, unless the context requires otherwise, the word "comprise", or variations such as "comprises" or "comprising", will be understood to imply the inclusion of a stated integer or group of integers but not the exclusion of any other integer or group of integers.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

EXAMPLES

The following methods serve to more fully describe the manner of using the above-described invention, as well as to set forth the best modes contemplated for carrying out various aspects of the invention. It is understood that these methods in no way serve to limit the true scope of this invention, but rather are presented for illustrative purposes.

Example 1

Detecting Protein Modifications in a Biological Sample

Materials/Methods (i) Labels

Fluorescent Label 1 (F1) was BODIPY TMR cadaverine-IA (TMR, excitation 545 nm; emission 571 nm) and Label 2 (F2) was BODIPY FL C1-IA (FL, excitation 503 nm; emission 512 nm) (Molecular Probes). Each fluorescent label contains an iodoacetamide group covalently linked to a fluorescent BODIPY moiety. A carboxamidomethylation reaction of the iodoacetamide group to the free thiol groups of cysteine residues was carried out at pH 7.5 followed by covalent linkage.

(ii) Labelling

Jurkat cells+/−2 mM $H_2O_2$ for 5 min in HBS buffer were extracted with RQB buffer (20% TCA in acetone, to trap thiol redox state) by resuspending the cells, using sonication (1×10 sec burst) and incubating the samples at −20° C. for 2 h. The RQB was removed by washing the protein pellet with ice cold acetone and protein samples were resuspended in MSS buffer (8M urea, 10 mM EDTA, 50 mM HEPES, 4% CHAPS and 1% pH3-10 IPG buffer at pH=8).

The first label (F1) was added to the samples for 2 h enabling it to react with exposed thiol groups on proteins (prot-SH) in the samples. Unreacted label (F1) was removed by centrifuging through a Sephadex G-25 spin column (3.5 cm pack height) at 1000 g for 4 min.

The samples were then treated with the reducing agent 2-carboxyethyl phosphine (TCEP)) for 10 min to reduce protein disulfides (prot-SSG) to protein thiols (prot-SH). The second label (F2) was added with TCEP and incubated for 2 hours to react with newly exposed thiol groups (prot-SH).

Proteins were then separated on two dimensional electrophoresis gels (2D PAGE). The labelled proteins run together during 2D PAGE because they have comparable isoelectric points and molecular masses. A fluoroimager (ProXpress Scanner) was used to locate proteins containing the fluorescent labels. An automated spot detection program (ProGENESIS) was used to quantify the signal of the reduced and oxidised proteins. For each labelled protein spot, a ratio of reduced to oxidised cysteine can be calculated.

Results

Figure 1B:
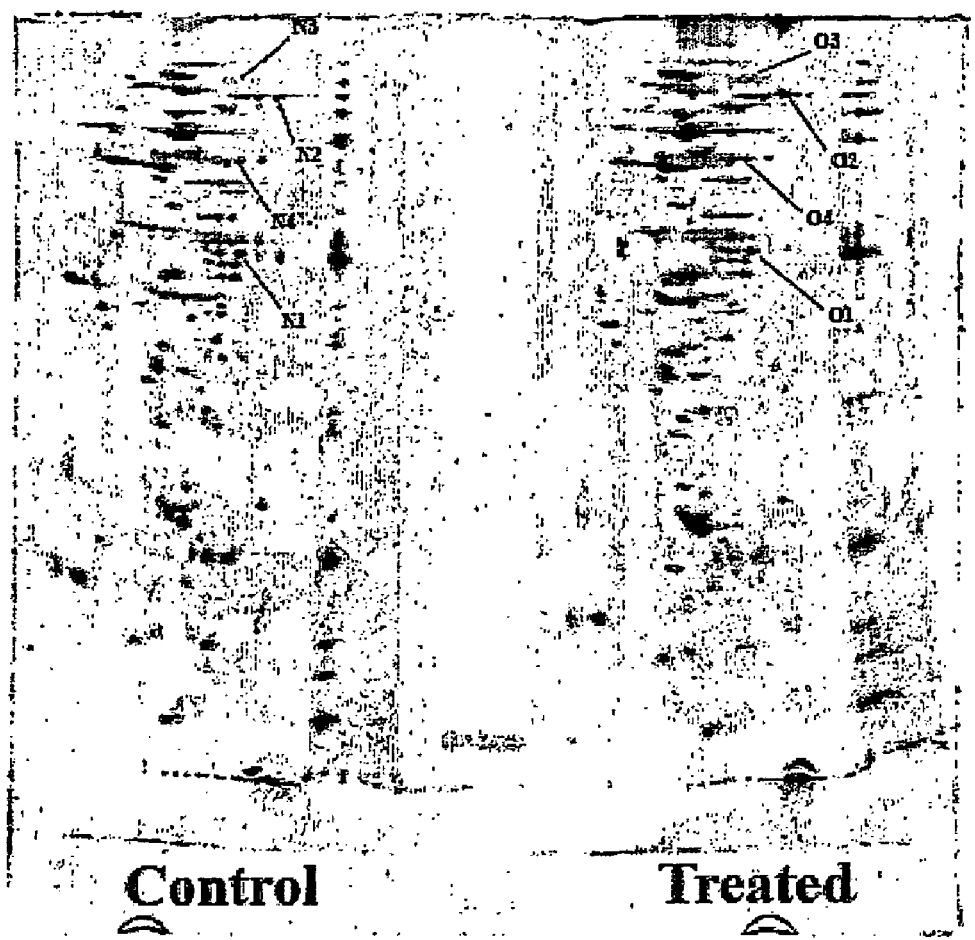
FIG. 1B shows the Sypro Ruby scan of the same gel after post-staining with the total protein stain Sypro Ruby.

The fluorescent ratio of the two labels was found to differ for several proteins (FIG. 1A). Comparable total protein staining with Sypro RUBY for each spot indicated that these changes were not a result of differential loading of protein samples (FIG. 1B).

Four proteins (N1-4) were selected from the 2D gel because of differential staining and thus potential changes in their oxidised/reduced state caused by exposure to $H_2O_2$. Their corresponding spots on the treated sample (O1-4) were also picked. Proteins were excised from the gel and digested with trypsin.

Analysis was carried out using electro-spray time-of-flight mass spectrometry (ESI-MS). Proteins were identified with the Mascot Peptide Search database search and results were returned as the highest probably match. Table 1 shows a list of probable proteins that were detected as having possible redox modification due to treatment of Jurkat cells with 2 mM $H_2O_2$.

TABLE 1

| Spot Number | Protein Identified | Mass | Peptides Matched | Mascot Score |
|---|---|---|---|---|
| N1, O1 | Heterogeneous nuclear ribonucleoprotein homolog JKTBP | 33568 | 4 | 136 |
| N2, O2 | Far upstream element binding protein 1 (FUSE binding protein 1) | 67431 | 13 | 529 |
| N3, O3 | HSU94832 NID | 73116 | 17 | 656 |
| N4, O4 | Alpha enolase | 47008 | 7 | 343 |

Example 2

Analysis of Protein Modification in a Standard Protein Mixture

A set of standard proteins with known amounts of natural reduced and oxidised cysteine residues were analysed using an embodiment of the present invention.

Materials/Methods

A mixture of 25 µg each of BSA, AD, CA, OV, PEP, CytC, Cat, SOD and Lyz, were initially labelled with 1 mM label F1 for 2 h. F1 was removed and then the proteins were reduced using 5 mM TCEP and labelled with the 1 mM label F2 (in the presence of 5 mM TCEP).

Table 2 sets out the thiol properties of these proteins.

TABLE 2

| Protein | Abbrev | FW (kDa) | S—H | S—S | Total S—H | pI |
|---|---|---|---|---|---|---|
| cytochrome c (bovine) | CytC | 11.6 | 0 | 1 | 2 | 8.5-10 |
| lysozyme (chick egg white) | Lyz | 14.3 | 0 | 4 | 8 | 11.4 |
| superoxide dismutase (bovine) | SOD | 15.5 | 1 | 1 | 3 | 5.4-6.4 |
| carbonic anhydrase (bovine) | CA | 29.0 | 0 | 0 | 0 | 6-7 |
| alcohol dehydrogenase (yeast) | AD | 36.7 | 8 | 0 | 8 | 5.4-5.8 |
| pepsin (ovine) | PEP | 41.4 | 1 | 3 | 7 | 3 |
| ovalbumin (chick) | OV | 42.8 | 4 | 1 | 6 | 5 |
| catalase (bovine) | Cat | 57.6 | 4 | 0 | 4 | 5.4 |
| albumin (bovine serum) | BSA | 69.3 | 1 | 17 | 35 | 5.3 |

Results

Figure 2:
FIG. 2 shows ProXpress fluorescence scans of an SDS-PAGE gel of mixture of 25 µg each of BSA, AD, CA, OV, PEP, CytC, Cat, SOD and Lyz, mixed together and initially labelled with 1 mM TMR for 2 h, then reduced using 5 mM TCEP and labelled with the second label, 1 mM FL, showing that the reduced and oxidised cysteine profile of standard proteins can be observed on a single 2D PAGE.
Figure 2:
Figure 2:
Figure 2:
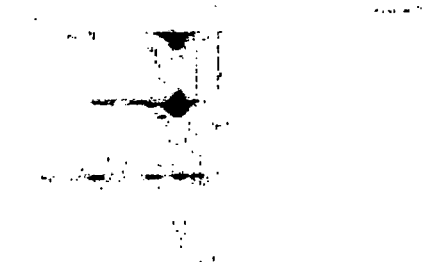

ProXpress fluorescence scans of an SDS-PAGE show that the reduced and oxidised cysteine profile of standard proteins can be observed on a single 2D PAGE. FIG. 2A shows a F1 scan of the 2D SDS-PAGE, FIG. 2B shows the same gel scanned at F2 wavelengths while FIG. 2C is a merged image of FIGS. 2A and B. Both reduced and oxidized proteins were detected with this approach.

Example 3

Identification of Proteins Undergoing Redox Changes Following a Change in the Oxidising Environment Materials/Methods The fluorescent dyes, BODIPY® FL N-(2-aminoethyl) maleimide (FLm, Tag 1) and BODIPY® TMR $C_5$-maleimide (TMRm, Tag 2) were used in a method to identify proteins undergoing thiol redox changes following a change in the oxidising environment.

Cells were divided into three groups and treated as follows:
A. standard culture conditions
B. exposed to oxidising conditions (20 µM $H_2O_2$ for 5 minutes); and
C. exposed to a reduced oxygen concentration (10-20 µM) relative to standard culture conditions (where oxygen concentration is 203 µM) for 10 minutes.

Figure 3:
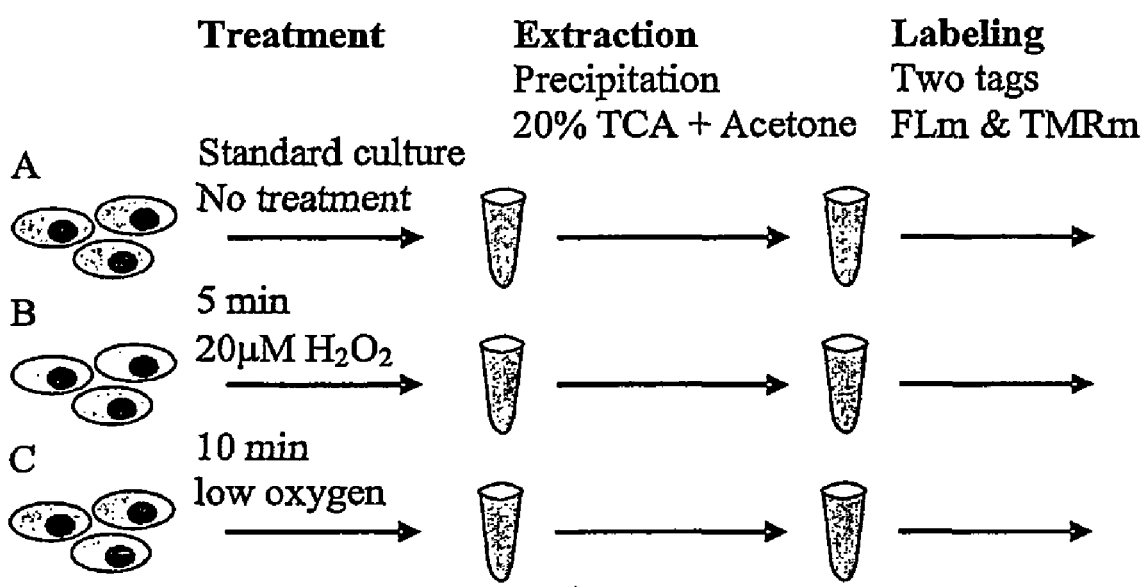
FIG. 3 is a schematic depiction of the protocol used to demonstrate one embodiment of the present invention capable of identifying proteins undergoing thiol redox changes following a change in the oxidising environment.

The protocol, schematically reproduced in FIG. 3, was repeated over four separate experiments: With respect to the different treatments, three comparisons are possible: standard conditions to low oxygen (protocol A to protocol C); oxidising treatment to standard conditions (protocol B to protocol A); and $H_2O_2$ treatment to low oxygen (protocol B to protocol C).

The parameters for labelling of samples with the FLm and TMRm were established from testing a mixture of known proteins with various numbers of thiol groups and oxidised disulfides. In these studies FLm and TMRm were used at the amount of 10 nmol in a final reaction volume of 300 µl.

Following labelling the samples were prepared in a buffer (8M Urea, 4% CHAPS) with 2% IPG Buffer pH 3-10. The sample was then loaded onto the IPGPhor (GE) for isoelectric focusing. An 18 cm immobiline pH 3-10 strip (GE) was used together with a standard protocol setting for the IPGPhor. At the end of isoelectric focusing, strips were equilibrated (6M Urea, 2% SDS, 300 mM Tris pH 8.8, 20% glycerol, 2.5% acrylamide) for 20 min, 25° C. The strips were then loaded onto 12.5% SDS-PAGE for mass separation.

Results 2D gels were scanned with a fluorescent gel scanner (Typhoon TR10, GE) and imaging software (Progeneis, Non-linear) was used to analyze spot volume at each fluorescent wavelength. Each gel was scanned using 2 specific laser and filter settings (for FLm: PMT=470V, Ex=Blue Laser (488 nm), Em=520 BP 40 nm, for TMRm: PMT=420V, Ex=Green Laser (532 nm), Em=580 BP 30 nm).

Figure 4:
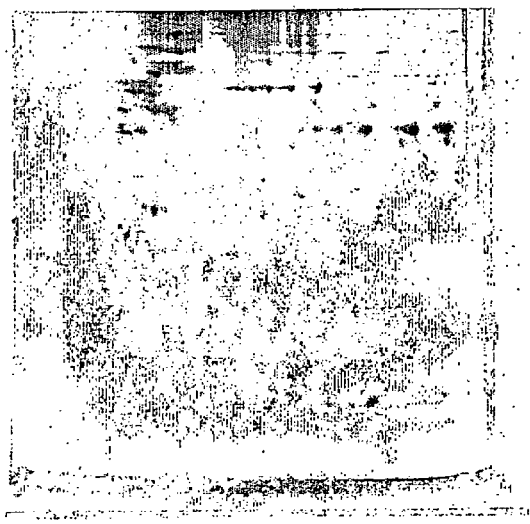
FIG. 4 depicts gel images taken from a standard (no treatment) cell preparation. Spots visible following labelling with FLm (A) indicates the presence of free thiol groups. Spots visible following labelling with TMRm (B) indicates the presence of disulfide groups. Gels were also stained with coomassie (C). Spots chosen for analysis are shown by circles (D).
Figure 4:
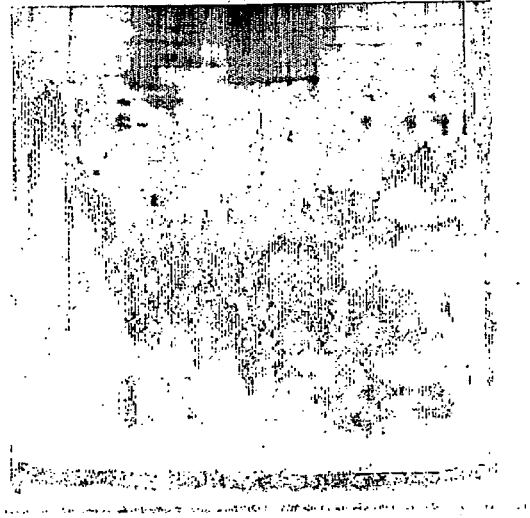
Figure 4:
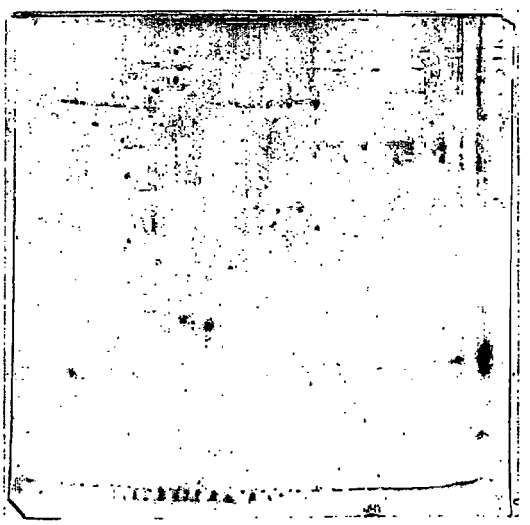
Figure 4:
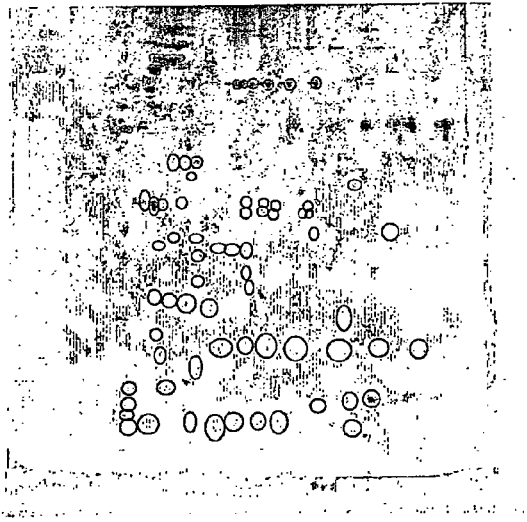

Gel images were analysed from 4 separate experiments with each experiment consisting of the same 3 protocols (A, B and C) with 2 gel images generated for each gel (FLm and TMRm). A total of 24 gel images were generated (4×3×2). For each gel, Progenesis detected 800-1200 spots tagged with FLm and 800-1200 spots tagged with TMRm. Example gel images are shown in FIG. 4.

Figure 5:
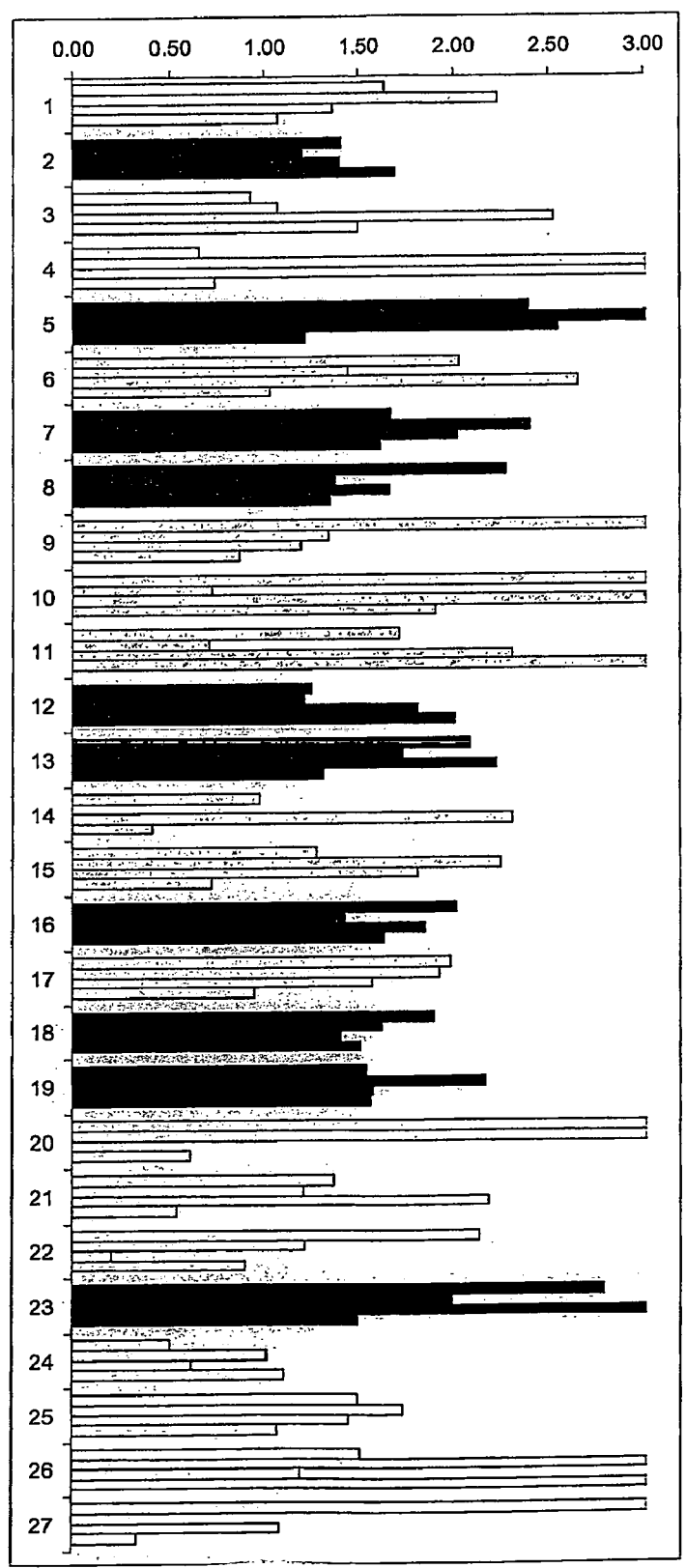
FIG. 5 is a graph illustrating the comparison ratios for comparison 3 ($H_2O_2$ treatment to low oxygen, protocol B to protocol C). The cut off for criteria 1 required that the comparison ratio had to be greater than 1 across all of the experiments). The cut off for criteria 2 required that the comparison ratio had to be greater than 1.2 across all of the experiments. Spots meeting criteria 2 are shown in red.

For maximum accuracy, spots were analysed manually. For each comparison (eg protocol A to protocol C) there were 4 experiments with two gel images (FLm and TMRm) to give a total of 8 gel images (4×2). Seventy nine representative spots were chosen for analysis, as manual analysis was time consuming and a large number of gel images needed to be analysed (FIG. 5). Spots were chosen on the basis that they appeared on at least six of the eight images and that they were not streaked on any gel.

The signal for TMRm and FLm for each spot was estimated following background subtractions using the "Average of Spot Parameter" mode. For each matched spot a ratio of TMRm/FLm (tag 2/tag 1) was calculated. Note that the spot ratio does not give any information about the degree to which the protein is oxidised. That is, a spot ratio of 1 does not mean the protein is 50% oxidised.

The following spot ratios (TMRm/FLm) for spot 33 are set out in Table 3 hereunder.

TABLE 3

| Protocol | Expt #1 | Expt #2 | Expt #3 | Expt #4 |
|---|---|---|---|---|
| A (Standard) | 0.87 | 0.63 | 0.58 | 0.99 |
| B (oxidising) | 1.55 | 1.98 | 1.35 | 1.58 |
| C (Low oxygen) | 0.32 | 0.62 | 0.53 | 1.05 |

Examination of the table shows that protein spot 33 was oxidised when comparing oxidising conditions to standard conditions but not when standard conditions were compared with low oxygen conditions.

To compare protocols, a comparison spot ratio was calculated from spot ratios. Matched gel sets were performed for each experiment, so it was appropriate to calculate comparison spot ratios for each experiment. For example, for spot 33 comparison 1, expt #1, (A/C) gave the following: 0.87/0.32=2.7

The following formulas were used for the comparisons:
Comparison 1—protocol A to protocol C=Standard spot ratio/low oxygen spot ratio;
Comparison 2—protocol B to protocol A=oxidising spot ratio/normal oxygen spot ratio; and
Comparison 3—protocol B to protocol C=oxidising spot ratio/low oxygen spot ratio.

For spot 33 the following data (Table 4) were generated

TABLE 4

| Comparison | Expt #1 | Expt #2 | Expt #3 | Expt #4 |
|---|---|---|---|---|
| 1 (A/C) | 2.7 | 1.0 | 1.1 | 0.9 |
| 2 (B/A) | 1.8 | 3.1 | 2.3 | 1.6 |
| 3 (B/C) | 4.8 | 3.2 | 2.6 | 1.5 |

A number greater than 1 indicates the spot is relatively more oxidised in the first treatment relative to the second treatment.

We chose two criteria to identify proteins responding to changes in oxidising conditions (FIG. 5). For criteria 1, the comparison ratio had to be greater than 1 across all of the experiments. For each comparison, involving eight gels, not all spots could be analysed, so some spots were only analysed for three experiments, involving six gels. Criteria 2 was more rigorous with requirement that the comparison ratio be greater than 1.2 across all of the experiments.

Figure 6:
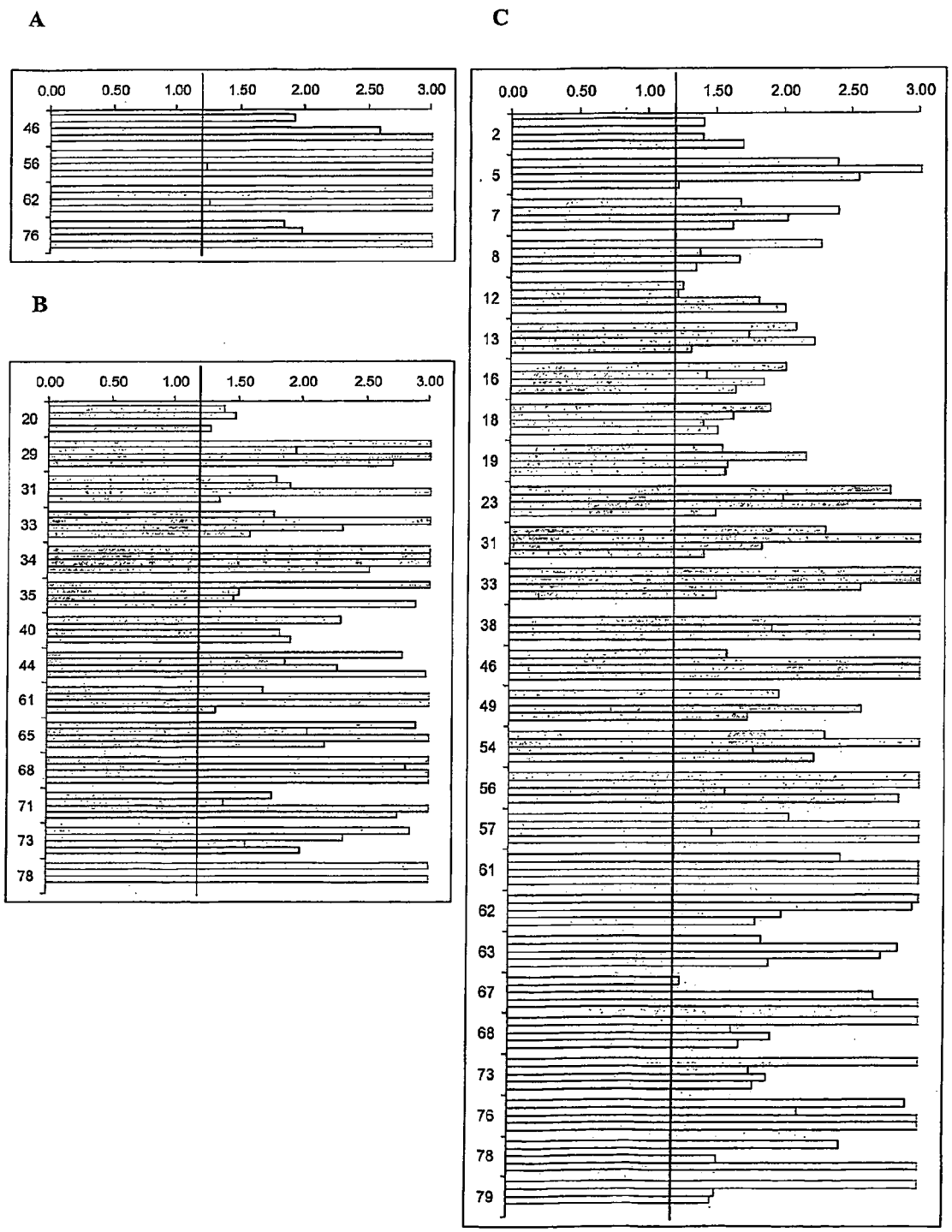
FIG. 6 is a series of graphs illustrating the comparison ratios. Only spots responding to changes in oxidising conditions are shown for changes meeting criteria 2 (the comparison ratio had to be greater than 1.2 across all of the experiments). The 1.2 cutoff is shown as a solid black line in each graph. A maximum comparison ratio of 3 is shown. A=Comparison 1—standard conditions to low oxygen (protocol A to protocol C); B=Comparison 2—oxidising treatment to standard conditions (protocol B to protocol A); C=Comparison 3—oxidising treatment to low oxygen (protocol B to protocol C).
Figure 7:
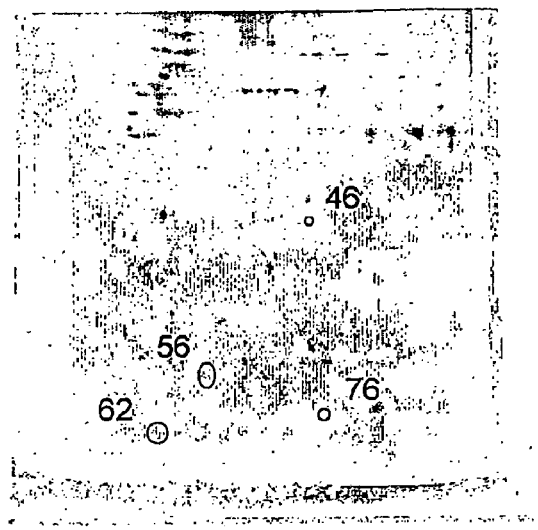
FIG. 7 is a series of gel images showing spots responding to changes in oxidising conditions. Spots are shown for changes meeting criteria 2, that is, the comparison ratio had to be greater than 1.2 across all of the experiments. A=Comparison 1—standard conditions to low oxygen (protocol A to protocol C); B=Comparison 2—$H_2O_2$ treatment to standard conditions (protocol B to protocol A); C=Comparison 3—$H_2O_2$ treatment to low oxygen (protocol B to protocol C).
Figure 7:
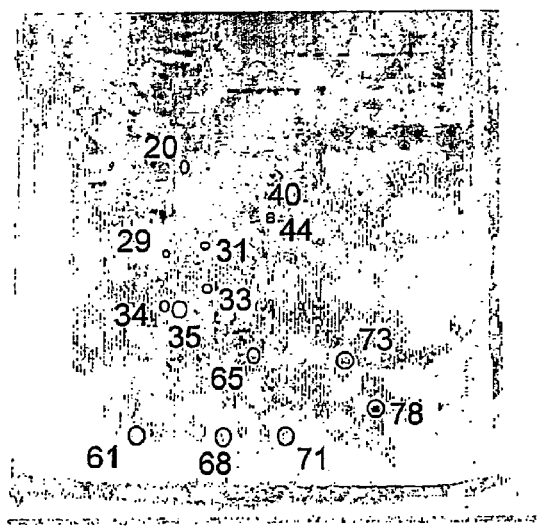
Figure 7:
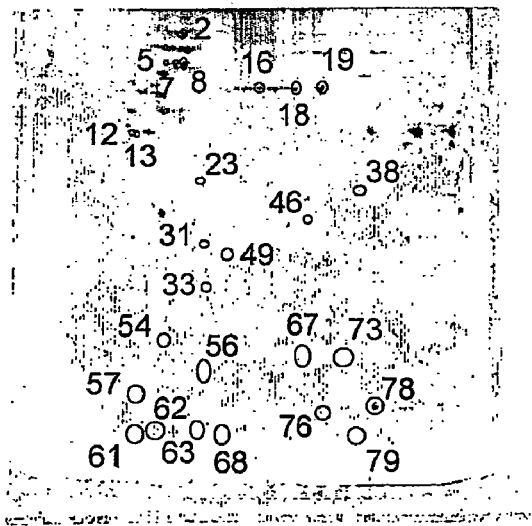

Using the two criteria, the number of protein spots responding to a change in oxidising conditions are shown in Table 5. The comparison ratios for individual spots are shown in FIG. 6 and the spots responding to changes in oxidising conditions are shown in FIG. 7.

TABLE 5

| | Criteria 1 | | Criteria 2 | |
|---|---|---|---|---|
| Comparison | # | % | # | % |
| Standard/low oxygen (78) | 9 | 11 | 4 | 5 |
| Oxidised/standard (77) | 21 | 27 | 14 | 18 |
| Oxidised/low oxygen (77) | 34 | 44 | 27 | 35 |

Total number of spots analysed in brackets. Number of spots (#) and percentage of spots (%) meeting each criteria (1 or 2) are presented. Note that the total number is less than 79 as some spots were not suitable for analysis with a particular protocol.

Modifications of the above-described modes of carrying out the various embodiments of this invention will be apparent to those skilled in the art based on the above teachings related to the disclosed invention. The above embodiments of the invention are merely exemplary and should not be construed to be in any way limiting.

The claims defining the invention are as follows:

1. A method for determining the redox status of a protein sample, the method comprising the steps of:
   a) contacting the sample with a first label adapted to bind to at least one reduced cysteine group therein;
   b) contacting the sample with a reducing agent to reduce at least one oxidised cysteine group therein;
   c) contacting the sample with a second label adapted to bind to any reduced cysteine groups produced in step (b); and
   d) determining the ratio of the signal from the first label to the signal from the second label wherein the ratio indicates the redox status.

2. A method according to claim 1 wherein the sample contains a single protein.

3. A method according to claim 1 wherein the sample contains a plurality of proteins.

4. A method according to claim 1 wherein the sample is a cell extract.

5. A method according to claim 1 wherein the sample is a tissue extract.

6. A method according to claim 4 wherein the sample comprises mitochondria.

7. A method according to claim 1 where in the method further comprises the step of comparing the ratio determined in step (d) to a reference ratio.

8. A method for determining the redox status of a plurality of proteins in a sample, the method comprising the steps of:
   a) contacting the sample with a first label adapted to bind to at least one reduced cysteine group therein;
   b) contacting the sample with a reducing agent to reduce at least one oxidised cysteine group therein;
   c) contacting the sample with a second label adapted to bind to any reduced cysteine groups produced in step (b);
   d) determining the ratio of the signal from the first label to the signal from the second label wherein the ratio indicates the redox status; and
   e) compiling the results from (d) into a profile containing the details of the redox status of proteins in the sample.

9. A method according to any one of the preceding claims further comprising the pre-treatment step of protecting reduced cysteine groups in the sample prior to labelling.

10. A method according to claim 9 wherein the protection is achieved by quenching all thiol-disulfide reactions.

11. A method according to claim 10 wherein the quenching comprises acid trapping the proteins.

12. A method according to claim 11 wherein the acid trapping comprises contacting the proteins with an appropriate buffer.

13. A method according to claim 12 wherein the buffer is RQB buffer (trichloracetic acid (TCA) in acetone).

14. A method according to claim 1 wherein the reduced cysteine group is a thiol group.

15. A method according to claim 14 wherein the thiol group is Cys-SH (cysteine residue) or Cys-SOH (sulfenic acid residue).

16. A method according to claim 1 wherein the oxidised cysteine group is selected from the group comprising: Cys-S—S—X; wherein S—X could be from the same protein, another protein or a small molecular mass thiol such as glutathione, Cys-SO2H, sulfinic acid; Cys-SO3H, or sulfonic acid.

17. A method according to claim 1 wherein the labels include a component adapted to bind to a reduced cysteine group and a component capable of emitting a signal.

18. A method according to claim 17 wherein the labels are adapted to bind covalently.

19. A method according to claim 17 wherein the component of the label adapted to bind to a reduced cysteine group is selected from the group consisting of:
   maleimide, phenylmercury, iodoacetamide, vinylpyridine, methyl bromide or iodoacetate or derivatives thereof.

20. A method according to claim 17 wherein the component of the label adapted to bind to the reduced cysteine group is iodoacetamide.

21. A method according to claim 17 wherein the component capable of emitting a signal is capable of being visualised.

22. A method according to claim 21 wherein the component is radioactive.

23. A method according to claim 21 wherein the component is fluorescent.

24. A method according to claim 23 wherein the component is a selected from the group comprising fluorescein, tetramethylrhodamine, Cye 3, Cye5 and Texas red, BODIPY, Oregon Green, eosin, pyridyloxazole, benzoxadiazole, Lucifer yellow, Alexa Flur, rhodamine and NANOGOLD.

25. A method according to claim 21 wherein the component is a protein.

26. A method according to claim 25 wherein the component is an antibody or an enzyme.

27. A method according to claim 1 further comprising the step of removing or inactivating the first label prior to addition of the second label.

28. A method according to claim 1 wherein the labels include a component adapted to bind to a reduced cysteine group and a component capable of being detected directly.

29. A method according to claim 28 where in labels are adapted to be detected using mass spectrometry.

30. A method according to claim 1 where the reducing agent is selected from the group comprising: cyteine, reduced glutathione, β-mercaptoethanol, thioglycollic acid, tributylphosphine, 2-carboxyethylphosphine (TCEP), dithiothreitol, sodium borohydride and sodium hydrosulfite.

31. A method for determining whether a protein sample has been modified by a protein modifying agent, the method comprising the steps of:
   a) contacting the sample with a first label adapted to bind to at least one reduced cysteine group therein;
   b) contacting the sample with a reducing agent to reduce at least one oxidised cysteine group therein;
   c) contacting the sample with a second label adapted to bind to any reduced cysteine groups produced in step (b); and
   d) determining the ratio of the signal from the first label to the signal from the second label and using said ratio to determine if the protein sample has been modified.

32. A method according to claim 31 wherein the protein modifying agent is a ROS or NO.

33. A method according to claim 32 wherein the ROS is capable of oxidising reduced thiol groups of cysteine residues to form disulphide bonds with glutathione, an adjacent cysteine or a small protein such as thioredoxin.

34. A method according to claim 32 wherein the ROS is selected from the group comprising: superoxide (O2-), hydroxyl radical (OH.), peroxyl radical (ROO.), alkoxyl radical (RO.), hydroperoxyl radical (HOO.), hypochlorous acid (HOCl), hydrogen peroxide (H2O2), ozone (O3), singlet oxygen (1O2) and peroxinitrite (ONOO).

35. A method for determining whether a protein sample has been modified, the method comprising the steps of:
   a) contacting the sample with a first label adapted to bind to at least one reduced cysteine group therein;
   b) contacting the sample with a reducing agent to reduce at least one oxidised cysteine group therein;
   c) contacting the sample with a second label adapted to bind to any reduced cysteine groups produced in step (b); and
   d) determining the ratio of the signal from the first label to the signal from the second label and comparing the ratio to a reference ratio to determine if the sample has been modified.

36. A method for assessing a ROS associated pathology or disease in a subject, the method comprising the steps of
   a) contacting a protein sample from the subject with a first label adapted to bind to at least one reduced cysteine group therein;
   b) contacting the sample with a reducing agent to reduce at least one oxidised cysteine group therein;
   c) contacting the sample with a second label adapted to bind to any reduced cysteine groups produced in step (b); and
   d) determining the ratio of the signal from the first label to the signal from the second label and using said ratio to determine if the sample has been modified.

37. A method according to claim 36 where in the pathology or disease is selected from the group comprising: stroke, heart attack and age-related degeneration, atherosclerosis, peripheral vascular occlusive disease, hypertension, alcoholic liver disease, angina, emphysema & bronchitis, chronic obstructive lung disease, Alzheimer's Disease, Parkinson's Disease, diabetes, cancer, liver transplantation related disease, coronary heart disease/heart failure, stroke/neurotrauma, cardiovascular disease, high blood pressure, hypoxia, fetal distress syndrome and sleep apnoea.

38. A method for assessing the efficacy of a therapeutic intervention for a ROS associated pathology or disease in a subject, the method comprising the steps of:
  a) contacting a protein sample from the subject with a first label adapted to bind to at least one reduced cysteine group therein;
  b) contacting the sample with a reducing agent to reduce at least one oxidised cysteine group therein;
  c) contacting the sample with a second label adapted to bind to any reduced cysteine groups produced in step (b); and
  d) determining the ratio of the signal from the first label to the signal from the second label and comparing said ratio obtained in the absence of the intervention with the ratio obtained in the presence of the intervention.

* * * * *